United States Patent [19]

Cormack et al.

[11] Patent Number: 4,863,275
[45] Date of Patent: Sep. 5, 1989

[54] PORTABLE, SHOCK-PROOF CONTAINER SURFACE PROFILING INSTRUMENTATION

[75] Inventors: Robert H. Cormack, Boulder; Carey S. Brown, Denver, both of Colo.

[73] Assignee: Ball Corporation, Muncie, Ind.

[21] Appl. No.: 264,203

[22] Filed: Oct. 28, 1988

Related U.S. Application Data

[63] Continuation-in-part of Ser. No. 183,763, Apr. 20, 1988.

[51] Int. Cl.⁴ ............... G01B 11/24; G01B 11/30; G01N 21/90
[52] U.S. Cl. .................. 356/376; 356/237; 356/428; 358/106
[58] Field of Search ............ 356/376, 237, 426, 428; 358/101, 106; 382/8; 209/577, 585, 597, 598

[56] References Cited

U.S. PATENT DOCUMENTS

| | | | |
|---|---|---|---|
| 3,666,885 | 5/1972 | Hemsley et al. | 178/6.8 |
| 3,826,576 | 7/1974 | Stewart | 356/384 |
| 4,021,119 | 5/1977 | Stauffer | 356/386 |
| 4,162,126 | 7/1979 | Nakagawa et al. | 356/237 |
| 4,226,539 | 10/1980 | Nakagawa et al. | 356/445 |
| 4,298,285 | 11/1981 | Ito | 356/376 |
| 4,326,808 | 4/1982 | Pryor et al. | 356/445 |
| 4,410,278 | 10/1983 | Makihira et al. | 356/445 |
| 4,466,937 | 8/1984 | Forbes | 250/560 |
| 4,476,533 | 10/1984 | Daudt et al. | 364/473 |
| 4,576,482 | 3/1986 | Pryor | 356/376 |
| 4,629,819 | 12/1986 | Clarke et al. | 356/237 |
| 4,675,730 | 6/1987 | Adomaitis et al. | 358/106 |
| 4,676,648 | 6/1987 | Schulz et al. | 356/426 |

Primary Examiner—F. L. Evans
Attorney, Agent, or Firm—Dorr, Carson, Sloan & Peterson

[57] ABSTRACT

A portable shock-proof instrument for determining the presence of defects in the surface profile of a container. The instrument includes a portable housing having shock-mounted therein an optical table carrying a point source of light, mirrors for reflecting the light in an inverted U-shaped path thereby providing compactness to the instrument, a lens in the middle portion of the U-shaped path for collimating the light and directing it past an edge of the container thereby producing a shadow image of the edge, a rotating stage for selectively turning the container, a cylindrical telescope for magnifying the horizontal field of view of the shadow image in order to enhance the detection of defects, and a camera for capturing a plurality of shadow edge images as the container is being turned. A processor is connected to the rotating stage and to the camera for analyzing the captured plurality of shadow edge images for the presence of defects.

18 Claims, 10 Drawing Sheets

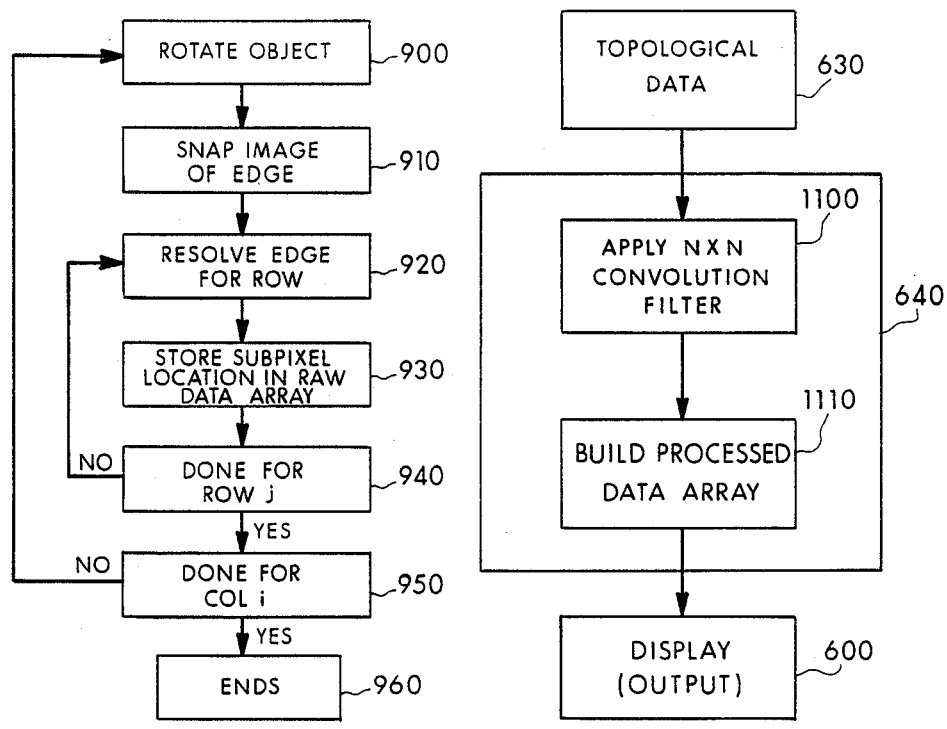
Fig. 9
Fig. 11
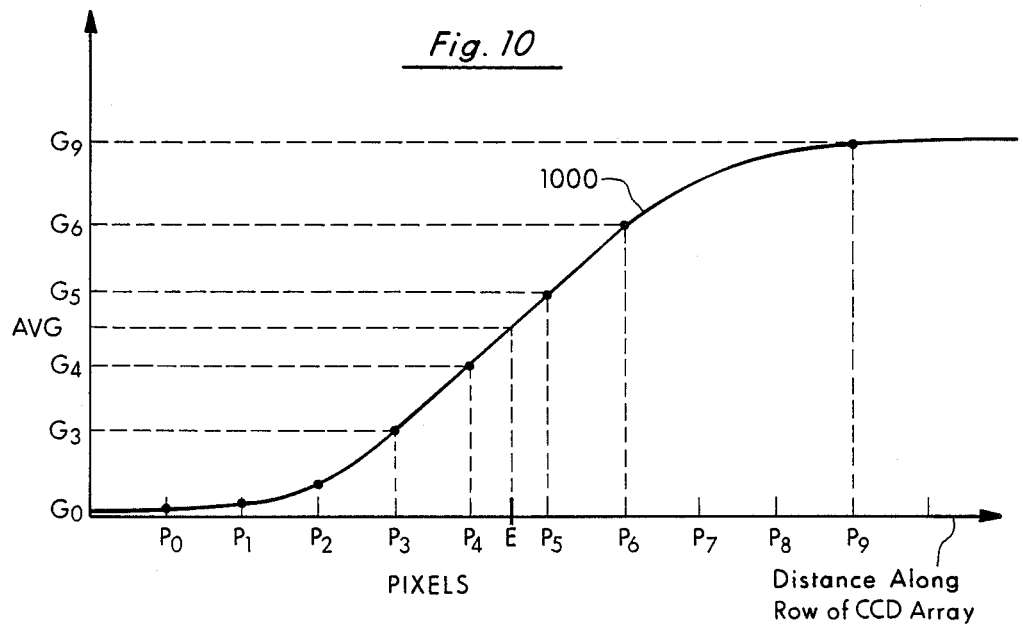
Fig. 10

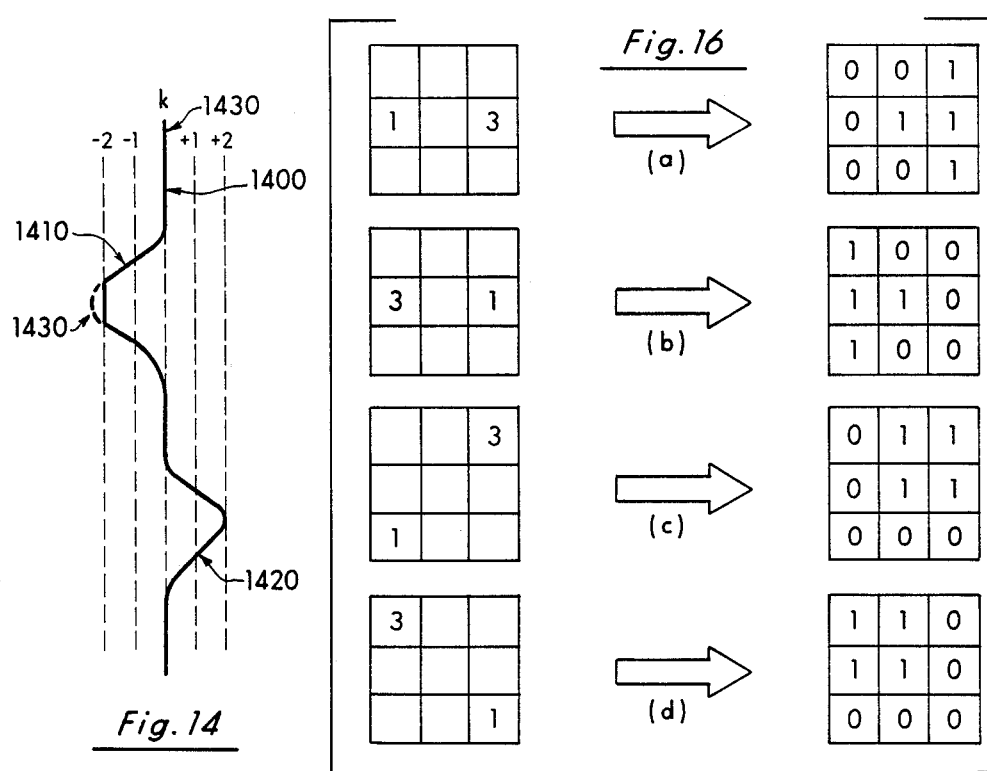

PORTABLE, SHOCK-PROOF CONTAINER SURFACE PROFILING INSTRUMENTATION

BACKGROUND OF THE INVENTION

1. Related Inventions

The present invention set forth herein is a continuation-in-part of "Optical Convex Surface Profiling and Gauging Apparatus and Method Therefor", Serial No. 07/183,763, filed Apr. 20, 1988.

2. Field of the Invention

The present invention relates to systems and methods for optically profiling and gauging convex surfaces of objects and, in particular, the present invention relates to a portable, shock-proof instrument that provides optical, non-contact profiling of the convex surface of containers such as beverage cans wherein the container is back lit with collimated white light and the resulting shadow image edges are detected and analyzed.

3. Statement of the Problem

There is a need in industry to profile the convex surfaces of containers to ascertain the presence of defects, to aid in the understanding of the manufacturing or shipping processes on the container, or to better analyze the material properties of the container.

For example, aluminum beverage cans are containers having a convex surface around their entire cylindrical sidewall which may be as thin as 0.005 inches. Conventional surface profiling techniques can provide precise measurements of unfilled beverage cans utilizing contact techniques, but such techniques are principally limited to the measurement of the top edge and bottom edge of the sidewall since contact with the center thin sidewalls of the can may cause deflection and, therefore, error in measurement. Hence, a need exists to profile the surface of aluminum beverage cans and to provide accurate metrology of the entire can sidewalls so that important information concerning the measurement and quantification of defects such as dents, may be obtained. Such information provides valuable feedback in understanding, evaluating, and adjusting the manufacturing processes to form the can as well as providing information concerning the material properties of the material, such as aluminum in such manufacturing processes.

While the present invention is generally directed towards the surface profiling of aluminum beverage cans, it is to be expressly understood that any convex surface or portion thereof of a container, work piece, or object could be likewise evaluated under the teachings of the present invention.

A number of prior art patented approaches are available for surface profiling such as the following which all relate to an optical reflection technique wherein light, usually a laser beam, is reflected off of the surface of the object. The reflected light is then analyzed. Examples of reflected light approaches are as follows.

U.S. Letters Patent 4,629,319 by Clarke et al. sets forth an invention for the electro-optical sensing of defects such as dents, creases, low spots and flat spots on the surface of sheet metal or plastic panels such as those used on the hoods and fenders of cars, refrigerators and furniture. Clarke directs light onto the surface. The light reflected from the surface impinges upon a retro-reflective member to return the reflected light to the surface area to be re-reflected. The re-reflected light is then imaged and carries information as to the nature of the defect.

U.S. Letters Patent 4,326,808 issued to Pryor et al. sets forth an apparatus for determining defects in the outer surface of an elongated object wherein the object to be inspected passes through an aperture of a conical mirror surface. The light is directed onto the mirror surface, reflected by the object, imaged and then analyzed to determine the nature of the defect.

U.S. Letters Patent 4,675,730 issued to Adomaitis sets forth an apparatus for continuously inspecting the surface of a moving object for defects. The surface of the object is illuminated with both specular and/or diffused light of selected wavelengths. The moving surface is rendered momentarily motionless and a plurality of sensors located to view the width of the object detects the presence of the defects. An electronic image of the defect contains gray scale levels that represent varying intensities of the light reflected by the defect. A comparison is then made with a defect free image and, if different, then a freeze frame analysis of the object is made.

U.S. Letters Patent 4,410,278 issued to Makihira et al. sets forth an apparatus for inspecting the outer peripheral surface of a cylindrical object. The light, in slit form, is projected on the surface of the cylindrical object. The reflected light is detected by a photo detector and is quantized at threshold values higher or lower than an average level. The three types of surface defects of a chip, a crack, and a pit are separately detected and identified.

U.S. Letters Patent 4,226,539 issued to Nakagawa et al. also sets forth a system for cylindrical body surface inspection. The cylindrical body is rotated around its axis at a constant speed. Light is directed onto the surface of the body and an optical detector detects the reflected light indicative of a surface condition of a small width baseline which is parallel to the axis of the cylindrical body. A sampling detection repeats as the body rotates to scan the entire surface of the cylinder.

U.S. Letters Patent 4,162,126 issued to Nakagawa et al. sets forth a camera system which senses diffused reflected light from the surface of an object in order to analyze the reflected light wherein a threshold level is used so that surface defect patterns such as a broken cavity, a pit, or a crack pattern can be selectively discriminated.

All of the above represent prior approaches for surface profiling and gauging involve a non-contacting system like the present invention. However, each of these approaches analyze light which is reflected from the surface and they are suitable for evaluating concave surfaces. The present invention does not reflect light nor does it analyze the reflected light.

The following prior art approaches set forth in inspection techniques which analyze the shadow of the object being inspected.

U.S. Letters Patent 4,576,482 issued to Pryor sets forth an apparatus for determining accurate dimensions of individual work pieces. The apparatus is a non-contacting system wherein a collimated or semi-collimated light source illuminates at least one edge of the work piece with parallel light rays so that a lens can form an image of the illuminated edge. This image provides an average shadow over an area of the edge. An array of photosensitive elements such as photodiodes produce an electrical signal in response to the light impacting thereon. The edge image as sensed by the photodiode array can then be analyzed to provide a determination of a dimension such as length, squareness, curvature and the like.

The 1972 patent to Hemsley (U.S. Letters Patent No. 3,666,885) utilizes a strobe for directing a short duration light pulse onto the object to form a shadow image of the object in a camera. The camera is modified for single line scanning and produces a line waveform of the shadow image. The Hemsley approach is adaptable for either hot or cold objects being scanned. Hemsley utilizes a referenced object to determine the initial measurement and then compares the object being inspected to the measured value and records any differences in the line waveforms.

The 1984 patent to Forbes (U.S. Letters Patent No. 4,465,937) utilizes a light source mounted in a scanning head that is rotated about the object and which can be advanced along the length of the object to provide data pertaining to the entire peripheral surface of the object. Forbes utilizes a light source that provides a beam of light having a width greater than the width of the object being scanned so that as the light source is rotated around the object, deviations in the shadow's edge can be sensed by photo sensors and determined.

The 1984 patent to Daudt (U.S. Letters Patent No. 4,476,533) pertains to a non-contact optical gauger for measuring hot glassware articles while being manufactured. The system makes specific measurements of height, perpendicular, neck diameter, and height variation of the glassware article. Articles falling outside predetermined measurements are rejected.

A need exists for a portable instrument that can be used in a manufacturing environment for surface profiling of containers such as aluminum beverage cans and for the detection of defects therein. The instrument must be shock-proof and capable of operating in dusty environments.

4. Solution to the Problem

The above prior art approaches for surface profiling involve a non-contacting system utilizing the shadow image from light projected onto the container or object. The present invention is similar to these approaches but substantially improves upon them. The present invention is mounted in a portable shock-proof housing for use in a manufacturing environment. The present invention utilizes collimated white light in a reduced field of view to produce a sharp shadow image of the object's edge. The instrument automatically creates from a plurality of such shadow images a dense array of topological data having 2000 to 5000 individual data points per inch for the surface of the container being profiled without distorting the surface of the container through contact. The cylindrical telescope of the present invention narrows the field of view in the horizontal direction of the shadow image to magnify the presence of defects. This increases the accuracy of sub-pixel analysis of the present invention.

SUMMARY OF THE INVENTION

The portable, shock-proof instrument of the present invention is capable of operating in a manufacturing environment for determining the surface profile of a container and for analyzing that profile for the presence of any defects. The instrument includes a housing mounted on wheels containing internally therein a vertically mounted optical table positioned on shock-mounts.

Mounted on the optical table are a number of optical elements including a point source of light directed vertically upward in the housing, a first mirror on the table receptive of the light from the point source for reflecting the light by ninety degrees so that the reflected light is directed horizontally in the housing, a first lens mounted on the table for collimating the reflected light from the first mirror and for directing the collimated light past the edge of the container in order to produce a sharp shadow image of the edge, a rotating stage is also mounted on the table which firmly holds the container with a vacuum for selectively rotating the container, a second lens for focusing the collimated light carrying the shadow image, a second mirror for reflecting the light from the second lens ninety degrees downwardly in the housing, a pair of cylindrical lenses for magnifying the horizontal field of the shadow image in order to enhance the presence of any defects in the edge, a relay lens for accumulating all the light and to prevent light from further divergence, a field lens for receiving the real shadow edge image from the relay lens and for reimaging the shadow edge image to infinity, and a camera mounted on the table for capturing the plurality of real shadow edge images from the field lens as the container is rotated.

The mirrors are used to direct the light from the point source in an inverted U-shaped path on the optical table thereby allowing for compactness of design.

In the event of any shock to the housing, all of the optics contained on the table are insensitive to vibrations from the shock and the instrument is still capable of ascertaining the profile of the can.

In addition, a dust-proof housing is provided around the relay lens and the field lens in order to eliminate the presence of any dust which could affect the surface profile analysis.

Finally, a processor is connected to the rotating stage and to the camera for processing the captured plurality of shadow edge images. The processing includes the creation of a surface profile, the analysis of the surface profile through spatial filters, the classification of dents according to magnitude, and the mapping of the location, periphery, and area of the dents.

DESCRIPTION OF THE DRAWING

FIG. 9 is the flow chart setting forth the calculation of the sub-pixel values for each individual row and column location;

FIG. 10 is a graphical illustration showing the determination of the sub-pixel value for a discrete shadow edge value at a selected row and column in the surface profile;

FIG. 11 is a flow chart setting forth the spatial filtering performed by the present invention;

FIG. 14 is an illustration showing the truncation of pixels exceeding a predetermined value;

FIG. 16 is a chart of basic dent mapping tests of the present invention;

FIG. 17 is an example using the basic tests shown in FIG. 16 to locate and map a dent in a surface profile;

SPECIFICATION

Figure 1:
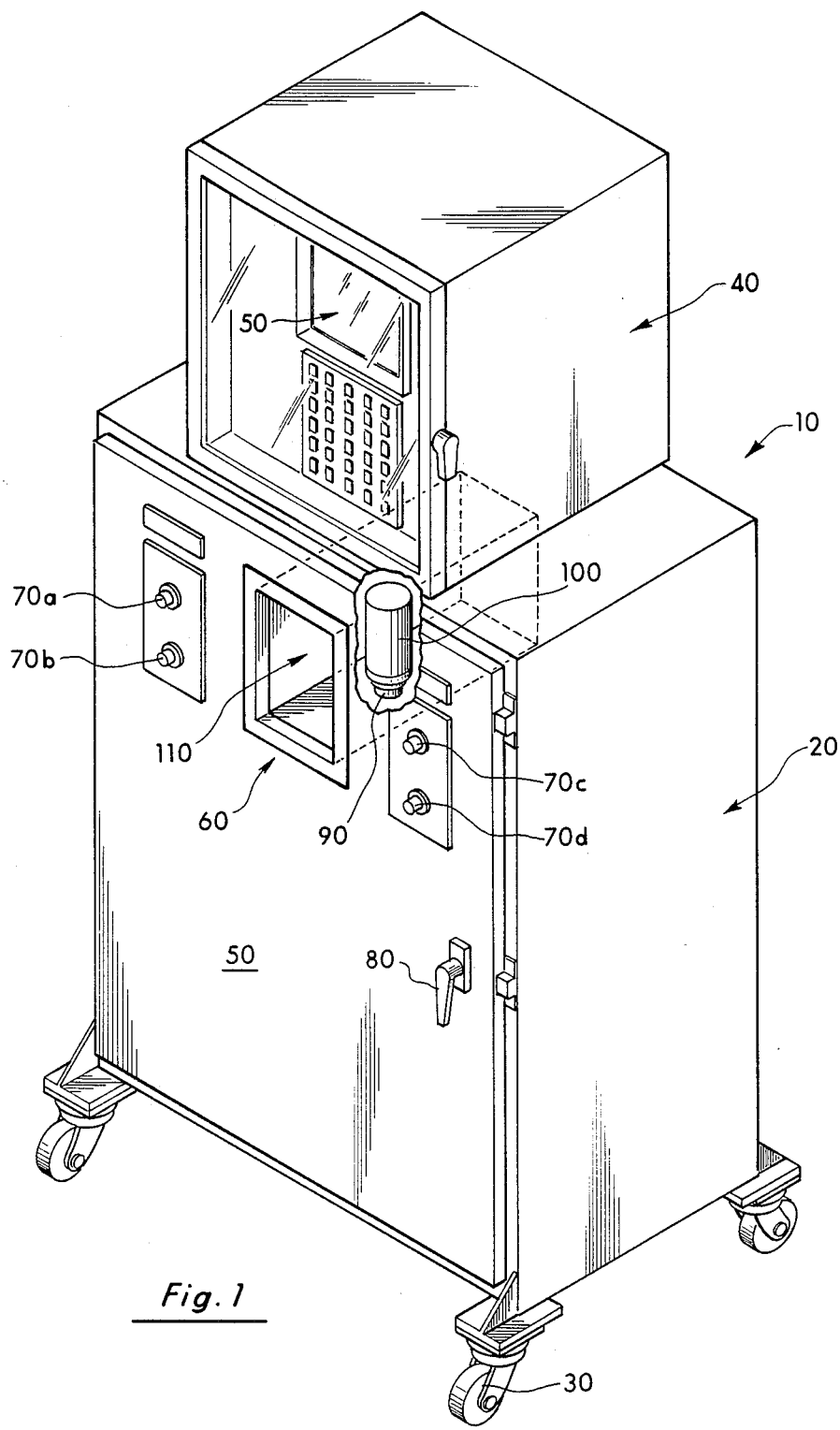
FIG. 1 is a perspective view of the portable, shock-proof surface profile instrument of the present invention.

In FIG. 1, the portable surface profiling instrument 10 of the present invention is shown having a housing 20 mounted on wheels 30. Placed on top of housing 10 or at another location is a processor 40 having a monitor 50 for viewing the surface profile of a container 100 such as an aluminum beverage can. The housing 20 has a door 50 which contains an opening 60. Also contained on door 50 are controls 70 for turning on the system power 70a, for turning on a motor 70b, for executing a run 70c, and for deleting a run 70d. Access to the interior of the housing 20 is by means of activating handle 80 on door 50.

To use the instrument 10 of the present invention, an operator places a container 100 into opening 60 and places it on a rotating stage 90. The opening 60 is the front portion of a chamber 110 having five interior walls which are painted flat black.

In operation, the operator presses the system power 70a to provide power to the instrument 10, activates the motor 70b so that rotating stage 90 commences to rotate container 100; and activates the run sequence 70c so that a surface profile of the container 100 is determined by the processor 40 and displayed in monitor 50. If desired, the operator may delete the run 70d and start the run over. Once a container 100 has been profiled, a new container can be placed through opening 60 into chamber 110 and that container can be profiled.

The instrument 10 is designed to be operated in an industrial environment and, therefore, must be thoroughly shock-proof so that bumps on the housing 20 do not affect the surface profiling of the container 100 during a run. In addition, the interior of housing 20 must be sufficiently dust proof so as not to interfere with the optics contained therein. The wheels 30 provide significant mobility to the instrument 10 so that it can be moved from location to location in a factory environment. Again, during such movement, the system must be sufficiently shock-proof so that, even though a run is not being executed, the components within housing 20 are not knocked loose from adjustment.

It is to be understood that the arrangement of the components shown in FIG. 1 represents only the disclosed approach and that other designs could be arrived at under the teachings of the present invention. For example, processor 40 could be incorporated into housing 20.

1. Shock-Mounted Optical Table

Figure 2:
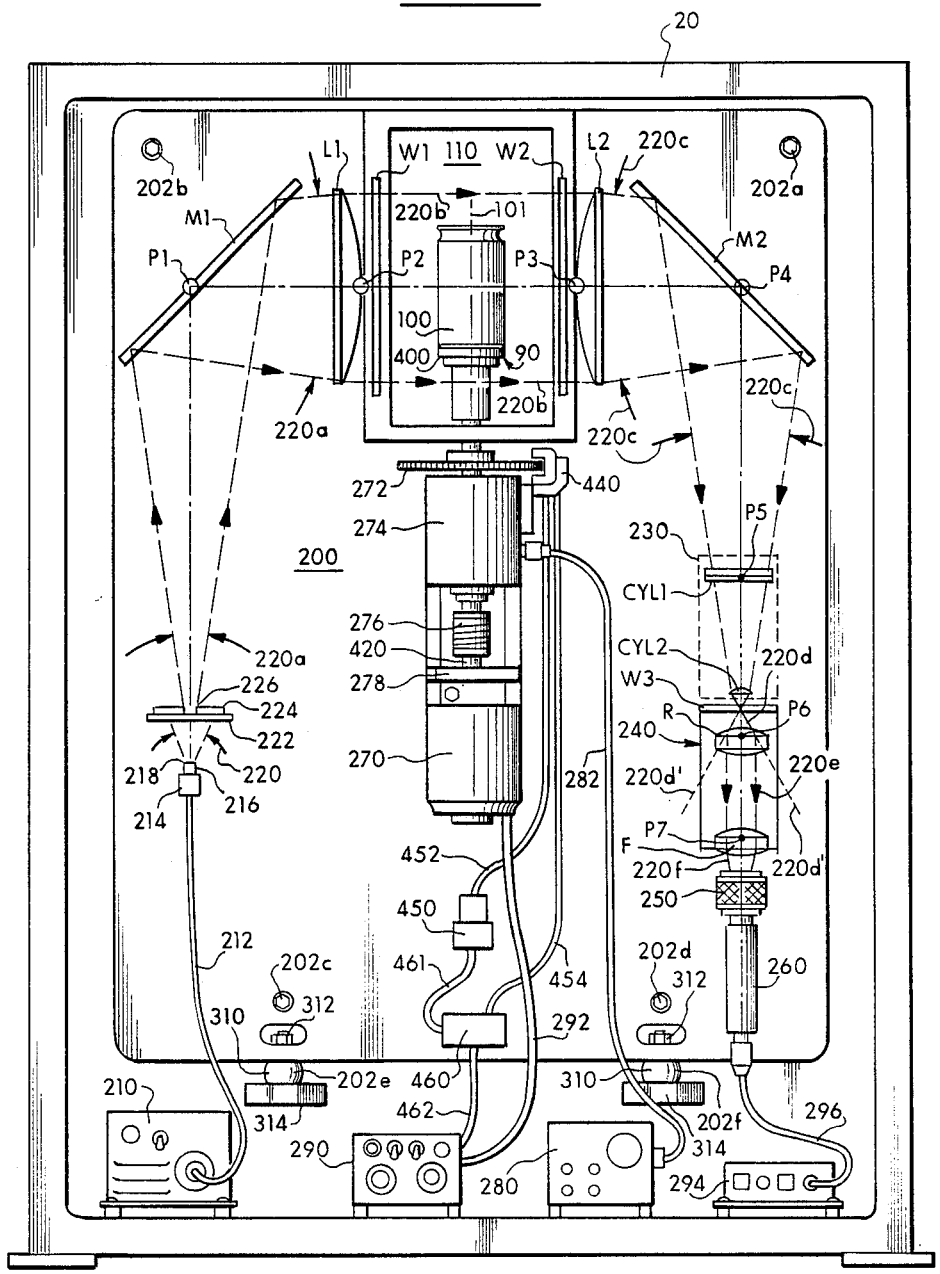
FIG. 2 is a side planar view of the optical table mounted on the interior of the housing of the instrument of FIG. 1.
Figure 3:
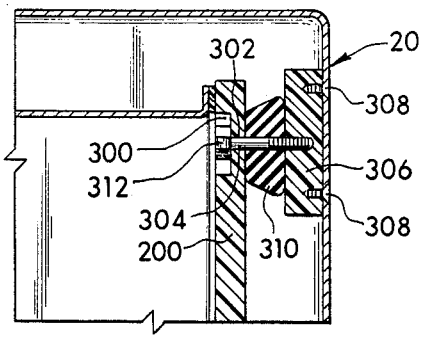
FIG. 3 is a cross-section showing a shock-proof mount of the present invention.

In FIG. 2, the optical table 200 is shown shock-mounted to the interior of housing 20. The optical table 200 is substantially rectangular in shape and is cut from ¾ inch thick aluminum plate. The optical table 200 is shock-mounted to the interior of the housing 20 at six points 202a through 202f. Horizontal shock mounts 202a through 202d hold the side of the table 200 to the interior of the housing 20. The details of each of the shock-mounts 202a–202d are shown in FIG. 3. The optical table 200 has a recess 300 and a hole 302 which receives a threaded bolt 304. The bolt threads into a block 306 which is affixed to the interior of housing 200 by means of screws 308. A rubber shock-mount 310 is disposed between the aluminum optical table 200 and the block 306. The head 312 of the bolt 304 firmly holds the plate to the housing 20.

Vertical shock-mounts 202e and 202f hold the plate 200 at the bottom to provide shock protection in the vertical direction. Each of these shock-mounts 202e and 202f utilize a rubber shock-mount 310 connected to a support plate 314 which is mounted to the housing 310 also by screws 308, not shown. As before in FIG. 3, a threaded bolt 304 engages block 314 and a nut 312 firmly holds the optical table 200 to the vertical shock-mounts 202e and 202f. In this fashion, any components mounted to the optical table 200 move in unison in the presence of vibration so that any vibration on the housing 20 does not affect the operation of the instrument 10 of the present invention.

It is to be expressly understood that the shock-mounting of the optical table 200, as shown in FIGS. 2 and 3, is one approach and that other approaches accomplishing the same function could be suitably designed.

2. Optics Layout

The layout of the optics is shown in FIG. 2. Mounted at the bottom of the housing 20 is a light source 210 which produces a concentrated source of white light. The white light is delivered through a fiber optic cable 212 to a fixture 214 mounted on the optical table 200. The fixture 214 holds the end 216 of the fiber optic cable 212 firmly in place on table 20 so that a point source 218 of light 220 is provided. The light 220 is directed through a frosted glass diffuser 222 having an iris 224. The iris 224 functions to reduce the number of ray directions for light 220. The size of the circular aperture 226 is such that it effectively produces a substantially point source for light 220. This light is shown as rays 220a in FIG. 2. In the preferred embodiment, the end 218 of the fiber optic cable 216 is positioned 1.75 inches from the circular aperture 226 of the iris 224. Aperture 226 is preferably ¼ inch to 1 inch in diameter.

The diverging light 220a from the point source 218 is then reflected by mirror M1 which is a flat rectangular shaped mirror, five inches by ten inches in configuration. Mirror M1 functions to turn light 220a by ninety degrees. The reflected light 220a enters lens L1 which is a plano convex lens eight inches in diameter having a focal length of 25 inches. In the preferred embodiment, lens L1 is manufactured from a suitable plastic material. The lens L1 directs the light 220b through a glass window W1 which is a circular window, nine inches in diameter, positioned on the side of the chamber 110. The light 220b at this point is collimated and is directed through the chamber 110 across the container 100 and through a second window W2 and into lens L2.

The circular windows W1 and W2 which are identical in shape protect the surfaces of the plastic lenses L1 and L2 from scratching. Since the instrument 10 is operated in a dusty environment, the windows W1 and W2 must be periodically cleaned by the operator of the system. If the windows W1 and W2 were not present, the lenses L1 and L2 would be coated with dust and could be easily scratched when cleaned. Hence the windows W1 and W2 function to prevent scratching of lenses L1 and L2 and further function to prevent dust from outside of the instrument 10 entering the interior thereof. Windows W1 and W2 could be eliminated, but then much more expensive lenses L1 and L2 made from glass would have to be used.

Lens L2 is identical to construction to lens L1 and the convergent light rays 220c from lens L2 is reflected by mirror M2 at a 90 degree angle downwardly into a first cylindrical lens CYL1 of a pair of cylindrical lenses 230.

At this point, it can be observed that mirrors M1 and M2 have reflected the light 220 in an inverted U-shape direction to allow the optics of the present invention to be compactly positioned on the optical table 200. Furthermore, the provision of the windows W1 and W2 are provided in the instrument 10 for the practical reasons of preventing damage to the plastic lenses L1 and L2 and to block the delivery of dust to the interior of the housing 20. Lens L1 functions to deliver light 220 past the container 100 and lens L2 then delivers the light into the cylindrical telescope comprising lenses CYL1, CYL2 R and F.

Cylindrical lenses CLY1 and CLY2 together form the objective lens 230 of the telescope 230, 240 which is inserted into the path of the light 220c. Cylindrical lens CYL1 has a 150 millimeter focal length and is a rectangular lens 60 millimeters by 50 millimeters. Cylindrical lens CLY2 has a shorter focal length of 60 millimeters and is a rectangular lens 60 millimeters by 20 millimeters. A distance of 5 ⅜ inches separates the two lens. The cylindrical lenses 230 are used to reduce or compress the field of view perpendicular to the rotation axis (i.e., the horizontal direction) of the container 100.

The light 220d delivered from the cylindrical lenses 230 enters a relay lens R which is contained in a dust-tight housing 240. A glass window W3 is mounted at one end of the housing 240 and the light 220d is directed through the window W3 and through a relay lens R. The window W3, in the preferred embodiment, is two inches in diameter.

The light 220e from the relay lens R is delivered into a field lens F which is mounted on the opposing end of the dust-tight housing 242. The relay lens R and the field lens F are each 50 millimeters in diameter and have a focal length of 75 millimeters. The light 220f from the field lens is then delivered into the camera lens 250 of the camera 260.

The relay lens R performs the important function of collecting all of the light 220d and focusing it into the camera 260. Without the use of the relay lens R, the light 220d would continue to diverge outwardly as shown by dotted lines 220d' and the camera 260 would not receive all of the light 220b directed past the container 100 and, therefore, the resolution would be decidedly affected. The relay lens R relays all of the light and directs it into the camera 260.

The housing 240 must be dust-tight since any particles of dust occurring between window W3 which is essentially located at the focal point of cylindrical lenses 230 and the field lens F would significantly affect the output of the instrument.

The camera 260 is preferably a CCD array camera made by Sony as Model No. XC-77. The camera incorporates a high quality lens 250 such a Fuji television 25 millimeter lens. The lens 142 is conventionally connected to the camera 140.

In the preferred embodiment, point P1 is located 17 inches from the aperture 226, point P2 is located 7 inches from point P1, point P3 is located 9 inches from point P2, point P4 is located 7 inches from point P3, point P5 is located 10 ½ inches from point P4, point P6 is located 7 ¼ inches from point P5, and point P7 is located 4 inches from point P6.

While the above is a preferred arrangement of the optics, it is to be expressly understood that changes or variations in the design of this layout could be made under the teachings of the claimed invention. For example, the light 220b directed past the container 100 could be slightly converging as taught by the above referenced parent application.

3. Optics Operation

The optics layout discussed above represents a compact and highly stable arrangement. It is to be expressly understood that other suitable layouts could be designed in accordance with the above teachings.

In comparison to the profiling engaging apparatus of the parent application referred to above, the optical layout of FIG. 2 is folded through use of mirrors M1 and M2 for compactness and for mounting into housing 20. In addition, two large plastic lenses L1 and L2 are used on either side of container 100 instead of the use of one Fresnel lens between the container and the light source. The two large plastic lenses L1 and L2 improve upon the parent approach by minimizing any non-uniform back lighting problems caused by flaws present in the Fresnel lens. In addition, the use of two lenses L1 and L2 allows the optical path to be shorter, thereby contributing to the compactness of the system. Finally, the use of two lenses L1 and L2 allows the light passing the container 100 to be accurately collimated (neither converging or diverging).

Hence, an exceptionally clean and accurate shadow of the container 100 is produced. Finally, the cylindrical telescope that the camera 260 looks through at the can has been redesigned. The telescope 230, 240 consists of two plano-convex cylindrical lens CYL1 and CYL2 and two bi-convex achromatic lenses R and F. As in the parent application, the telescope functions in the same fashion. That is to magnify the container horizontally in order to increase the resolution of small dents while maintaining a large enough field of view vertically to include the entire container. The advantage of the present approach is that large ratios of horizontal to vertical magnification are possible without interfering with the uniformity of the back illumination of the container.

In this approach, as shown in FIG. 2, the two cylindrically lenses CYL1 and CYL2 together form the object lens of a simple telescope. They are oriented on the optical table to produce a real image of the container from each lens CYL1 and CYL2 which appears at the position of the relay lens R. To accomplish this, cylindrical lens CYL1 has a longer focal length than the focal length of cylindrical lens CYL2. This causes the image of the container 100 to be magnified more in the horizontal direction than in the vertical direction.

The field lens F then reimages the real image of the container from lens R to infinity allowing the camera lens 250 to easily focus on the image. The camera lens 250 is adjusted to focus at infinity. Hence, the magnification is the ratio of the focal lengths of the objective lenses CYL to the field lens F. The objective lenses CYL, in the design of FIG. 2, consists of two cross cylindrical lenses with differing focal lengths. Hence, the magnification in the horizontal direction is the ratio of the focal length of lens CYL1 to the focal length lens F and in the vertical direction the ratio of focal length of lens CYL2 to the focal length lens F. The relay lens R has no effect on the magnification.

As mentioned, light 220d is focused somewhat ahead of the relay lens R. If relay lens R were not present, light 220d, would diverge enough, as shown by dotted lines 220d' so that a substantial amount of the light would miss lens F. This causes some of the background of the container 100 to appear dark instead of light in the camera image and thus would make the computer processing of the image difficult. The focal power of the relay lens R is chosen so that it redirects this light into the field lens F and hence back into the camera lens 250. This maintains the uniformity of the back illumination.

Since the relay lens R is actually in focus at the camera, any dust on this lens will show in the camera's image, seriously degrading the system's performance. This necessitates the use of a dustproof housing 240.

In the preferred embodiment, a four to one image magnification in the horizontal direction is desired and is believed to be a combinational effect of the cylindrical telescope, the camera 260, and the image capture process in the computer. The end result is to have a four to one magnification as processed by the computer.

4. Rotating stage

Figure 4:
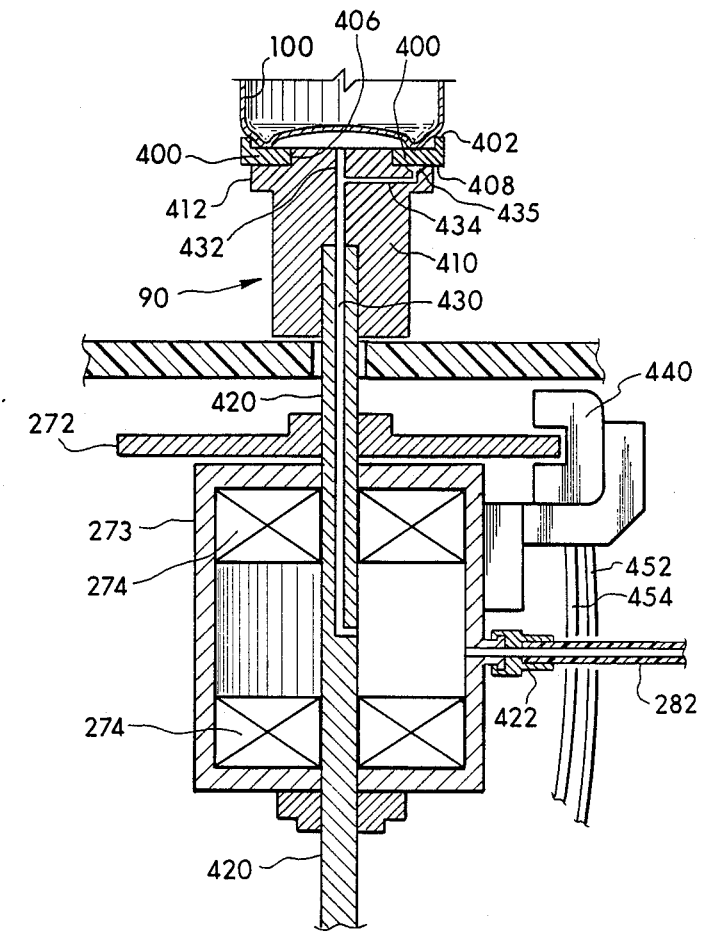
FIG. 4 is a cross-section showing the rotating stage firmly holding a container and the details of the vacuum system.

The rotating stage 90, as shown in FIG. 2 and as detailed in FIG. 4, includes an adaptor 400 which is designed to hold the bottom of the container 100. The adaptor in FIG. 4 is circular and has an outer upstanding lip 402. It is designed to engage the bottom of container 100 and, therefore, adaptor 400 can be suitably modified to hold many different shaped container bottoms. The adaptor 400 has a centrally formed annular region 406. The underside face 408 of the adaptor 400 is flat. The adaptor 400 rests on a coupler 410 which has a first ring 412 that uniformly abuts the flat surface 408 of adaptor 400. Coupler 410 is connected to a motor shaft 420 which comes from motor 270.

The coupler 410 is conventionally connected through a keyway, not shown, to the shaft 420. Also connected to shaft 420 is a gear 272, a bearing housing 273 containing a pair of bearings 274, a flexible coupler 276, and a gear box 278. The shaft 420 engages heavy duty bearing 274 which provides rotation to the container 100 without imparting vibration thereto. The flexible coupler 276 also isolates the rotating stage 90 from vibration.

As shown in FIG. 2, a vacuum pump 280 is provided which pulls a vacuum through tube 282. Tube 282 is connected to the bearing housing 274 by means of a coupler 422 as shown in FIG. 4. A formed passageway 430 is drilled in shaft 420 and through coupler 410. The formed passageway has two branches 432 and 434. Branch 432 provides a vacuum to the region between the coupler 410 and the bottom of the container 100 and branch 434 provides a vacuum to firmly hold the container adaptor 400 to the ring 412 of the coupler 410. A shallow groove 435 is formed all around the upper circular surface of coupler 410 to provide an area for the vacuum to work. In this fashion, the vacuum 280 provides a vacuum, such as 10 lbs., through the rotating stage to firmly hold the container 100 and the adaptor 400 to the coupler 410.

Hence, under the teachings of the present invention, a number of different container adaptors can be selectively used by the operator of the present invention to hold different types of containers to coupler 410 of the rotating stage 90. Both the adaptor and the container are firmly held to the coupler by the vacuum.

It is to be expressly understood in FIG. 4 that although a preferred approach to providing a vacuum to firmly hold the container 100 in position is shown, other techniques for holding the container 100 or different shaped objects to the rotating stage could be provided. In addition, while the use of an isolation coupler and heavy duty bearing to minimize rotational vibration is provided, other design techniques to minimize such vibration could also be utilized.

Furthermore, a speed control 290 is provided in the housing 20. The speed control 290 over cable 292 powers the motor 270 which in the preferred embodiment, is a DC motor.

A gear 272 having 128 teeth is connected to the shaft 420. A photo circuit 440 detects the position of each of the 128 teeth of gear 272 and is connected with light source 450 which delivers light through fiber optic cable 452 into the sensor 440. The received light is then delivered back through fiber optic cable 454 to an electronic circuit 460 which counts the received light pulses. In this fashion, the precise position of the container can be ascertained. For example, as the motor 270 moves the container 100 to the next position (i.e., 128th of a revolution) the camera 260 captures a shadow image of the edge of the container 100.

Finally in FIG. 2, the power supply 294 for the camera 260 is shown. The power supply delivers the power over line 296. The output from the camera 260 is delivered over 262 to the processor 40.

5. Electrical Circuit

Figure 5:
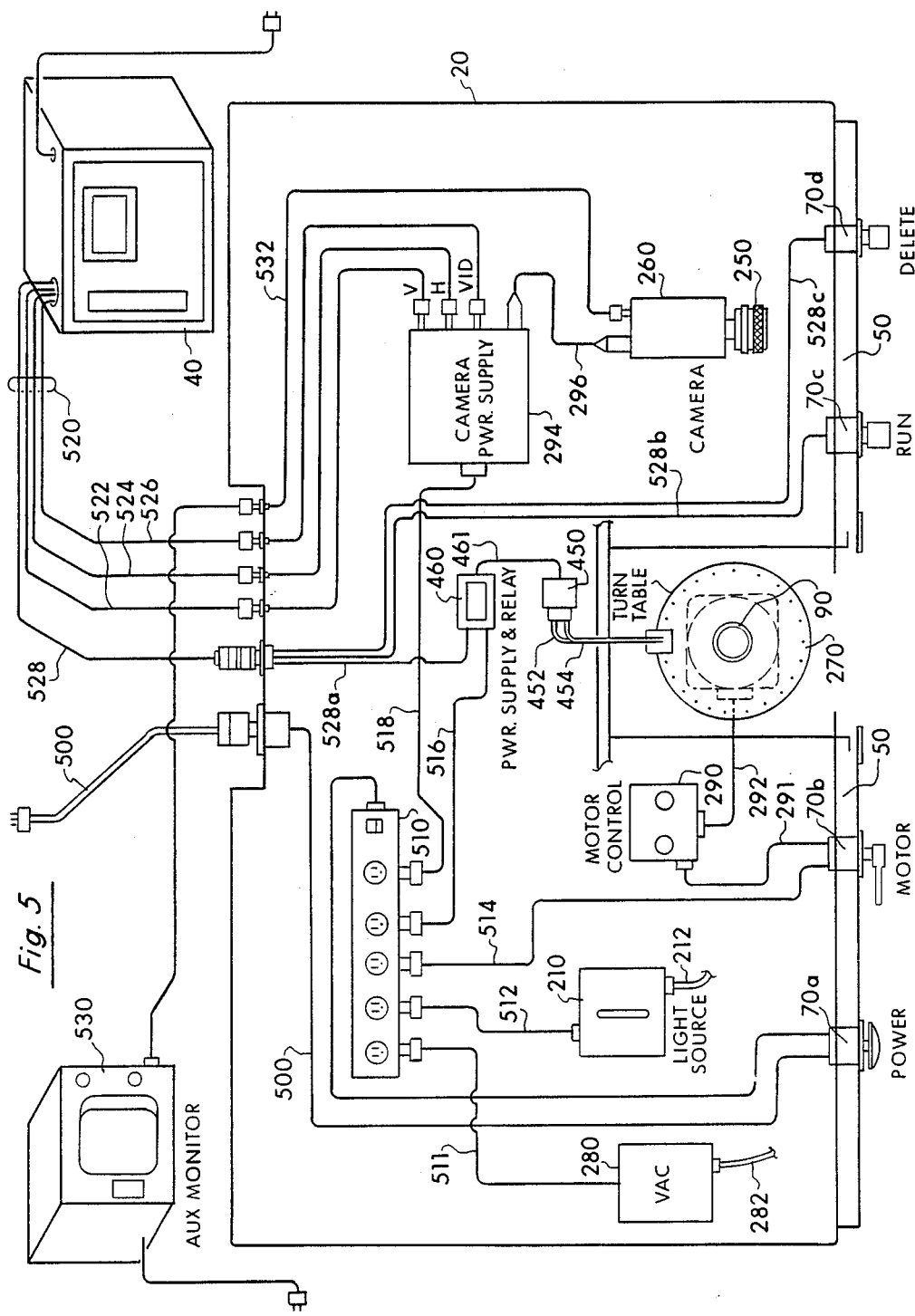
FIG. 5 is an electronic schematic showing the electrical interconnections of the various components of the present invention.
Figure 6:
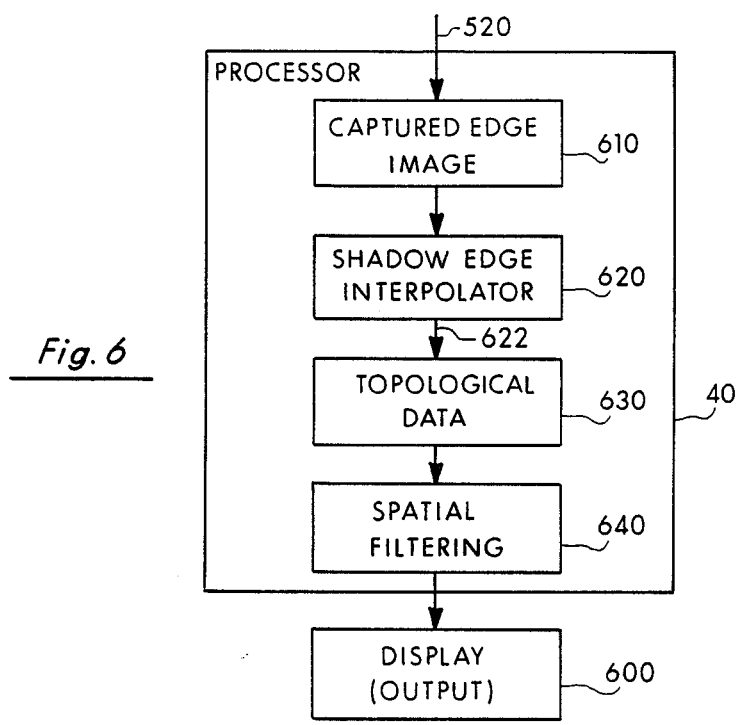
FIG. 6 is a flow chart showing the processing of the surface profile data by the processor of the present invention.

In FIG. 5, the electrical details for interconnecting the components of the present invention are shown. The power on-off switch 70a on housing cover 50 delivers power from a conventional line 500 to an outlet strip 510. The outlet strip 510 selectively delivers power to the vacuum 280 over line 511, the light source 210 over line 512 and to the motor on-off switch 70b over line 514. The motor on-off switch 70b in turn delivers power to the motor control 290 over line 291. The outlet strip 510 also delivers power over line 516 to the power supply and relay 460 which is interconnected to the sensor 45 over line 461. Finally, the outlet strip 510 provides power over line 518 to the camera power supply 294. The operator powers on the system by activating push button switch 70a and selectively turns the motor 270 on or off by means of activating switch 70b.

The processor 40 is connected to the housing 20 by means of cable 520. Processor 40 receives the vertical signal V from the camera supply 294 over line 522, the horizontal signal H over line 524 and the video signal VID over line 526. The processor 40 also communicates over bus 528 with the power supply relay 460 over line 528a, to the run switch 70c over line 528b and with the delete run switch 70d over line 528c.

An auxiliary monitor 530 can be provided which is interconnected over line 532 with camera 260 to view the camera video directly.

In operation, power is turned on by activating button 70a, the operator places the container 100 on the rotating stage 90 and the vacuum provided by the vacuum pump 280 firmly holds the container on the stage. The operator then activates the motor on-off switch 70b to cause container 100 to start rotating. As the stage 90 rotates, the sensor 450 senses the position of the rotation and delivers an appropriate signal over line 520a back to the processor 40 (for example, sensing the leading edge of a tooth in gear 272). When the operator is ready to capture images from the rotating container, the run button 70c is activated and the processor proceeds to capture shadow edge images of the container 100 as it is rotated at each of the detected timing intervals. At any time, the operator can delete a run by activating button 70b which commands the processor 40 over line 528c to stop capturing images.

While a preferred electrical circuit is shown and discussed above, it is to be expressly understood that variations thereto could be made by one skilled in the art.

6. Data Processing

The data processing system 40 of the present invention receives the captured shadow edge image 610 of the camera output over cable 520 and processes the image to provide the various displays 600 of the present invention.

The first step in processing the shadow images 610 from the camera 260 is to locate the edge of the shadow to much less than one pixel. This is performed by the shadow edge interpolator 620. Accuracies of up to one-/eightieth of a pixel have been obtained with the accuracy being limited only by the non-uniformity of the back lighting 120 and camera 260 noise.

The sub-pixel shadow locations 622 are arranged into topological data 630 which is an X-Y (row-column) data array. The topological data 630 represents the topological structure or surface profile of the object surface in sub-pixel values. Each column in the data array is a surface profile of edge 610 parallel to the axis 101 of rotation of the container 100. Each row of data represents a circumferential profile around one complete revolution or, in some cases, a partial revolution.

The X-Y topological data array 630 is then spatially filtered 640 for display 600. As will be discussed more fully, dents, pits, and other surface irregularities can be found and quantified by passing the topological data 630 through appropriate spatial filters. The filtered data 640 is delivered to the display system 600. As will be discussed further, graphical displays, because of the extensive amount of data generated, are the most effective way of presenting the data.

The present invention provides a substantial amount, such as 2000 to 5000, of individual data values corresponding to discrete physical points on the convex surface.

Figure 7:
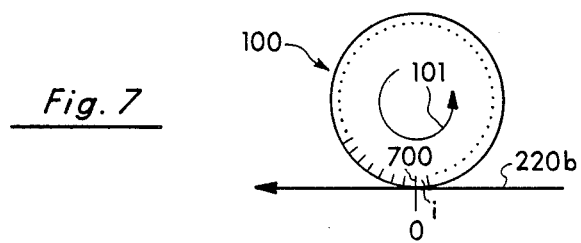
FIG. 7 is a top view illustration showing the container being rotated about the rotational axis to provide a plurality of shadow edges.
Figure 8:
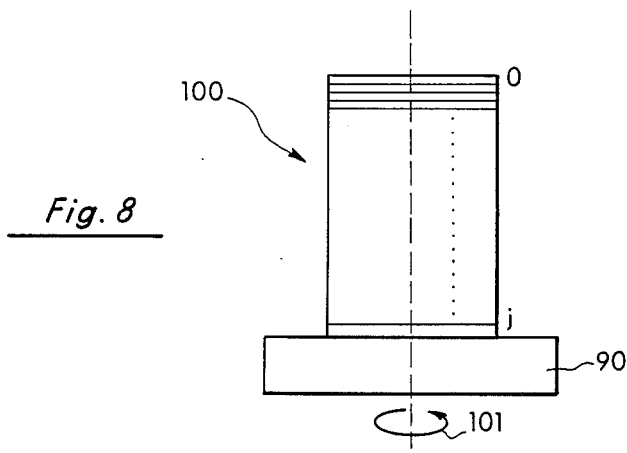
FIG. 8 is a side view illustration of the container of FIG. 7 being rotated about rotational axis 101 to provide a plurality of rows of surface profile information.

The container 100, as shown in FIGS. 7 and 8, can be defined to have a certain number of edges or columns. FIG. 7 shows a number of columns from 0 to i where the number of edges could, for example, be any suitable number such as 128 columns, 256 columns, or 512 columns. Likewise, the container has a number of rows such as that shown in FIG. 8 from 0 to j where j could equal 100, 200 or 400 under the teachings of the present invention. It is to be understood that this approach could be suitably adapted for a partial scan of container 100 or for an object other than a cylindrically shaped object shown in FIGS. 7 and 8.

The data gathering flow of the present invention is set forth in FIG. 9 and will be discussed with reference to FIGS. 7 and 8. The first step 900 in FIG. 9 is to rotate the container 100 and then during rotation to capture 910 an image of the edge in camera 260. In FIG. 7, the edge 700 is initially at position 0 and, therefore, a snap of the image at position 0 is taken. The shadow edge image taken at position 0 in step 910 actually contains a column of data points, o-j for each of the vertical and discrete columns, o-i. With respect to the image taken of column 0, the first row 0 has its data point edge resolved as will be discussed next a. Determination of Shadow's Edge

For example, and as shown in FIG. 10, if the shadow edge 700 for column 0, row 0 is shown as curve 1000, the determination or resolution of the actual edge could be done in a number of different ways. The present invention utilizes a "weighted local average" approach to ascertain the physical position of the container's edge from the captured shadow image 700. This sub-pixel edge location algorithm reduces noise in the processed image by a factor of two when compared with the "linear interpolation" approach set forth in the parent application. Curve 1000 represents the shadow edge at one vertical location (i.e., row), as sensed by the camera 260 as an analog signal.

Referring to FIG. 10, the shadow edge 700 is depicted as the continuous curve 1000 that increases from left to right. The pixel locations in one row of the video camera's CCD array are labeled along the horizontal axis (P0, P1, P2, etc.). The gray level value of each pixel is given by the intersection of each pixel's location and the shadow curve 1000. This gray level is labeled on the vertical axis (G0, G3, G4, etc.). The video signal is digitized into 256 gray levels from 0 to 255. An actual image of a shadow edge 700 will almost never span the complete 0 to 255 range of gray values.

To locate the edge roughly (to one pixel) the average gray value of the shadow edge is first calculated. This is done by averaging the gray level of a pixel far to the left of the edge with one far to the right of the edge such as for pixels P0 and P9. For example, the average gray level value (labeled AVG in FIG. 10) can be calculated by:

$$AVG = (G0+G9)/2 \qquad \text{Formula 1}$$

Next, the pixels whose gray values bracket the average value AVG are determined. In FIG. 10 the pixels on either side of the AVE value are P4 and P5 since:

$$G4 < AVG < G5 \qquad \text{Formula 2}$$

The next step is to locate the edge at a fraction of a pixel position. Assume the edge to be located at the position in the row of pixels where the gray value is equal to AVG. This position is labeled E in FIG. 10.

In this sub-pixel algorithm, to calculate the location of the edge E in FIG. 10 the equations would be:

$$\text{(location of } E) = \text{(location of } P4) + SUB', \text{ where:} \qquad \text{Formula 3}$$

$$SUB' = (AVG - Gavg4)/(Gavg5 - Gavg4) \text{ and:} \qquad \text{Formula 4}$$

$$Gavg4 = (1/4)G3 + (1/2)G4 + (1/4)G5 \qquad \text{Formula 5}$$

-continued
$$Gavg5 = (1/4)G4 + (1/2)G5 + (1/4)G6 \quad \text{Formula 6}$$

For example, assume the gray levels are:

$G0 = 40$ $G1 = 40$ $G2 = 40$ $G3 = 43$ $G4 = 51$ $G5 = 172$ $G6 = 242$ $G7 = 245$ $G8 = 245$ $G9 = 245$ then, $AVE = (40 + 245)/2 = 142.5$  FORMULA 1

$51 < 142.5 < 172$  FORMULA 2

$$Gavg4 = (43/4) + (51/2) + (172/4)$$
$$= 79.25$$
FORMULA 5

$$Gavg5 = (51/4) + (172/2) + (242/4)$$
$$= 159.25$$
FORMULA 6

$$SUB' = (142.5 - 79.25)/(159.25 - 79.25)$$
$$= 0.79$$
FORMULA 4 therefore:

$$E = (\text{Location of } P4) + SUB'$$
$$= 4.79 \text{ pixels}$$
FORMULA 3

It is to be understood that in the calibration of the optics and data collection 10 of the present invention that an initial physical calibration to a standard container 100 must be made to obtain the actual value of the distance along the horizontal axis of FIG. 10. Under the teachings of the present invention, the instrument 10 is such that one pixel equals seven mils on a conventional aluminum beverage can. Hence in the above example the distance is (4.79 ×7) =33.43 mils. It is to be further understood that the curve 1000 is an ideal curve and that the actual raw data is represented by pixels gray levels G0 –G9.

Returning now to FIG. 9, once the edge location E is determined for a given row of a shadow, the sub-pixel location is stored 930 in the raw data array and the routine ascertains whether all the rows are done 940. If not, the process of resolution is repeated until all rows are done. If all of the columns are not done 950, the container 100 is rotated (or rotates) to the next column, the edge shadow captured and the process repeats until all columns are done and then the routine ends 960.

This process may take six seconds to four minutes depending on the size of the container 100 and depending on how many columns and rows are required.

Under the teachings of the present invention, the rotating stage 90 operates asynchronously from the data processing. The camera 260 provides 60 frames per second and if 128 columns of the container 100 are analyzed, that means in ten seconds (the time for one complete revolution 62), 12.8 columns per second are produced. The camera is operating much faster at 60 frames per second and therefore, approximately five frames for each column are produced. Under the teachings of the present invention, the data processing system 20 selects one of those frames for analysis.

It is possible to design the system such that the data processing system synchronously controls the rotation of the stage 90 so that as the stage 90 is rotated an image is captured and analyzed before causing the stage 90 to rotate to the next column. Hence, under the teachings of the present invention, the stage 90 can operate either asynchronously or synchronously with the processor 40. It is to also be expressly understood that the rotating stage 90 could be driven by a continuous or synchronous motor and the light source 210 could be a strobe lamp which could be selectively flashed by the processor 40 to strobe.

Figure 13:
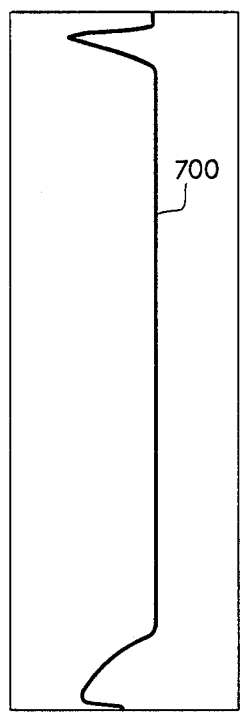
FIG. 13 is an illustration of an edge of a container received by the camera of the present invention.

In FIG. 13, the shadow image of a conventional aluminum beverage can edge 700 is drawn and is representative of the edge created by the instrument 10 of the present invention is shown. As mentioned, a large number of these images such as 128 images (corresponding to the columns) are taken to complete a surface profile. The data points on each edge constituting the rows are then calculated to sub-pixel accuracy as discussed above for the shadow edge interpolator 950.

Figure 18:
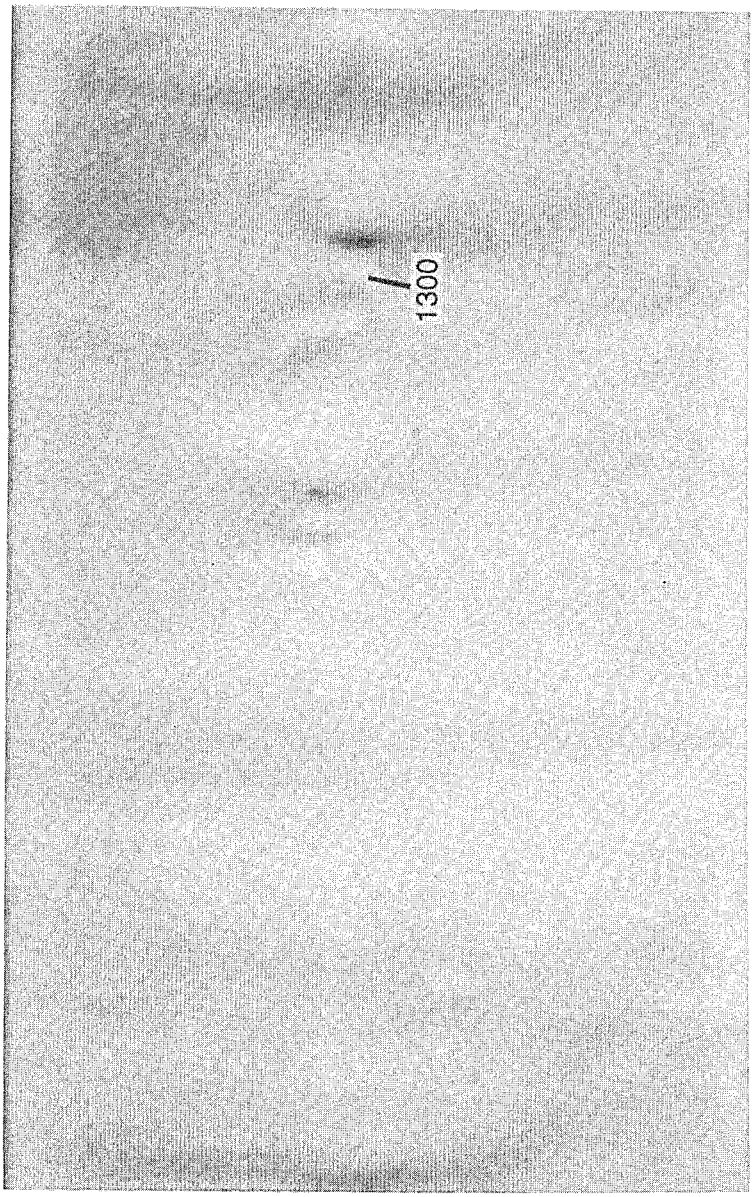
FIG. 18 is a photograph showing the raw pixel values of a surface profile.

FIG. 18 shows how the surface profile of data from the parent application in the data array can be displayed on a device (such as a video monitor 50) with a limited number of gray levels. Basically, a small range in the data can be expanded into the number of gray levels available and displayed on the monitor. Dent 1300 is illustrated. If the data extends beyond the range selected for display it can be truncated plus or minus, for example two pixels on either side of a gray value, k, as shown in FIG. 14. Dent 1410 is shown truncated 1430 whereas bump 1420 falls within the range. The filtering operation works on the data array, and so is independent of any choices made in this display technique.

b. Application of spatial Filters

In FIG. 11, details of the spatial filter 640 are shown. An "n ×n" convolution filter 1100 could be used on the raw profile data to emphasize the rate of change in the surface of the convex object. For example, the convolution filter could emphasize rates of change in the horizontal direction of the container 100, in the vertical direction of the container 100, or in both directions. For example, a suitable convolution filter could be a convolution kernel such as a LaPlacian edge detector. The convolution kernel can be matched to the object or to a standard set by the user of the system. The convolution filter modifies the raw data to emphasize the characteristic being analyzed (for example vertical dents). By tuning the convolution kernel for quickly changing slopes (i.e., serious dents), slow surface variations and changes are ignored and not displayed. This eliminates background noise.

Figure 19:
FIG. 19 is the profile of FIG. 18 processed through a spatial filter of the present invention.

The output of the convolution filter 1100 is delivered to a module that builds the data array 1010 based upon the output of the convolution filter. The results are then displayed 600. In FIG. 19, a graphical representation of the raw data of FIG. 12 after spatial filtering 170 by a suitable convolution kernel is displayed. The image is bright where the filter detects rapid changes in the container surface indicating dents. Dent 1300 is again shown.

The convolution process has been modified over the approach in the parent application so as to achieve a more uniform effect of the filtering on the top and bottom of the data array.

c. Adding Top and Bottom Rows to the Surface Profile

Figure 12:
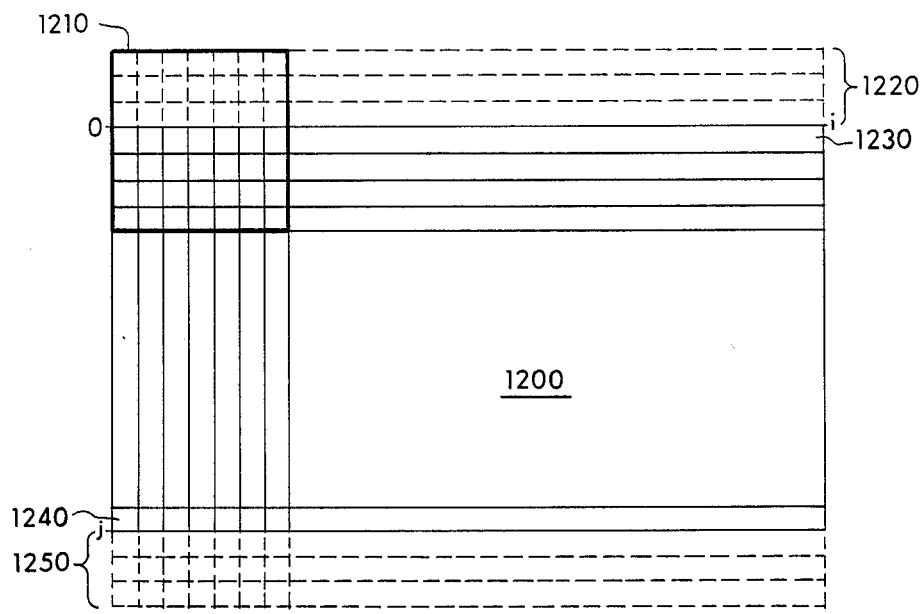
FIG. 12 sets forth the technique of the present invention of performing a "n ×n" convolution on the surface profile data.

Because a finite convolution filter determines a value in the output array based on a neighborhood of values in the input array, the beginning and end of the data cannot be filtered since those data points do not have complete neighborhoods. Several rows at the top and bottom of the array (representing the top and bottom of the inspected area of the container) do not have complete neighborhoods. Exactly how many rows are affected is dependent on the size of the convolution filter kernel —that is, the size of the neighborhood used for the filtering. For a "5 ×5" filter, the top two and bottom two rows do not have a sufficiently large neighborhood to be filtered. In general, for an "n ×n" kernel filter, the number of rows affected at the top and bottom will be $(n-1)/2$. Hence, for a "7 ×7" filter, n =3. In FIG. 12, the surface profile data array 1200 has o-j rows and o-i columns. A "7 ×7" kernel filter 1210 does not have a complete neighborhood since in the position shown in FIG. 12 no data is present in the missing rows 1220.

The left and right columns of the data array, however, are not affected. Since the data on each row represents a complete circle around the container, the left and right edges of a row represent contiguous points on the container; hence, the neighborhood of a data point on the left edge of the array includes points on the right edge of the array and vice-versa.

In order to extend the effect of the filter thereby increasing the accuracy, for example, the "7 ×7" filter 1210, to the top and bottom rows 1230 and 1240, two things are performed by the present invention. First, the data in the top row 1230 of the measured surface profile is copied to the three preselected additional rows 1220 above the start of the measured data. Likewise, the data in the bottom row 1230 is copied to the three preselected additional rows 1250 below the end of the measured data. Second, the convolution process is started with the convolution kernel centered on the first element of the measured data and ended with the kernel centered on the last element of measured data. This results in the filtered data array being the same size as the (unmodified) measured data array. Because of the copied data, the effect of the filter changes somewhat at the top and bottom of the array, becoming more one dimensional. This change occurs smoothly, however, and does not effect subsequent steps in the data processing.

d. Classification of Dents

Figure 15:
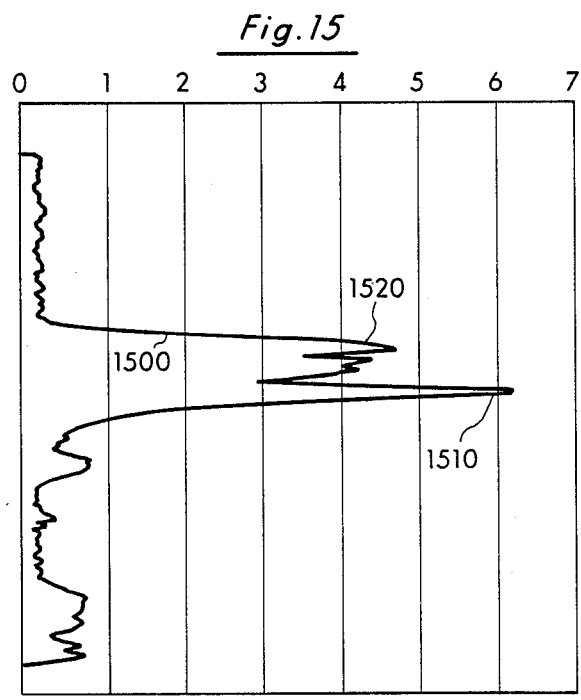
FIG. 15 is a graphical illustration of the magnitude of dents uncovered in the analysis of a selected container.

In FIG. 15, a graphical example 1500 an output of the present invention is shown. A convenient scale from 1 to 10 is chosen as a classification indicating severity of dents located vertically along edge 700 of the aluminum beverage can independent of the column location. The vertical scale of the graph of FIG. 15 represents the vertical height of the can and the dents found at each height throughout all columns of the can is plotted horizontally against the 1 to 10 scale.

FIG. 15 shows that dent 1510 has a magnitude 6 as graphically shown at 1400 and several dents 1520 of a magnitude between 4 and 5. Any suitable range of dent depths could be chosen for display on the scale. This graphical representation shown in FIG. 15 enables the system of the present invention to quickly classify containers based upon severity of dents. It also shows the physical location of the dents along the vertical height of the container and, therefore, provides substantial information as to the material make-up of the container and the effect of various manufacturing processes on the container as the container is being manufactured.

e. Mapping of Dents

The present invention also uses the following algorithm which searches for gradients in the filtered data array that exceed a pre-determined threshold. When the difference between two neighboring data points in the surface profile exceeds this threshold, the local area is marked as a dent. The exact value of the threshold used depends on the convolution kernel used to filter the original data and on the noise level in the data. The marking is done by adjusting the values in a binary-valued array that is the same size as the data array. A value of 1 signifies the area of a dent, and 0 signifies no dent at that location. The size of the local area that is marked for each instance of a higher-than-threshold gradient is chosen to produce a smooth, well-connected image of the dent.

Typically, a block of six data points that is offset towards the direction of increasing data values is used. This is shown in FIGS. 16 and 17. In FIG. 16, four of the eight possible cross block difference tests are illustrated for a 3 ×3 filter. For example, if the threshold difference is 2 (for purposes of illustration arbitrary values are used -in actuality the gray scale values are used) and the opposing values of 1 and 3 are in the block data points shown in FIGS. 16(a)–(d) then the block points are filled in with ones in the patterns shown. In FIG. 17(a), an illustration of a matrix of data points in a surface profile is shown. If the tests of FIG. 16 are applied, the resulting "1s" field showing the location, shape and area of the dent is shown in FIG. 17(b). From this the centroid of the dent can be calculated. Changing the difference value, increases or decreases the area of the dent being mapped.

In FIG. 17a, a block 1700 highlighted in a thick line, having the following representative pixel values, is shown:

```
              2 3 4
              1 2 2
              1 1 1
```

This block passes two of the eight cross-block tests where the difference exceeds "two":

```
   — 3 —                    — — 4
   — — —      and           — — —
   — 1 —                    1 — —
``` which creates two patterns of "ones":

```
   1 1 1                    0 1 1
   0 1 0      and           0 1 1
   0 0 0                    0 0 0
``` which when combined together creates a final pattern of markers for block 1700:

```
              1 1 1
              0 1 1
```

The block 1700 is then moved upwardly as shown by the dotted lines 1710 and the process repeats until the map of FIG. 17(*b*) is produced.

It is to be expressly understood that the rate of change or second derivative could also be used. In this event, rate of change would be the basis for the tests of FIG. 16.

Hence, the present invention provides a number of useful outputs including the actual surface profile, the surface profile processed by selected spatial filters, the classification of the magnitude of dents, and the location, shape and area of dents.

While preferred embodiments of the present invention have been shown, it is to be expressly understood that modifications and changes may be made thereto and that the present invention is set forth in the following claims.

We claim:

1. A portable shock-proof instrument for determining the presence of defects on the surface of an object, said instrument comprising:
   a housing (20),
   an optical table (200) shock-mounted in said housing, said table comprising:
   a. means (216, 224, 226) for producing a point source of light (220*a*),
   b. means (M1, M2) receptive of said light from said point source for reflecting said light in an inverted U-shaped path, said path having a first portion, a middle portion, and a third portion,
   c. means (L1, L2) for directing said reflected light in said middle portion of said path, said directing means directing said light (220*b*) past an edge of said object thereby producing a shadow image of said edge,
   d. means (CYL 1-2, F, R) receptive of said light in said third portion of said path for collecting substantially all of said light from said point source,
   e. means (260) for capturing a plurality of said shadow edge images from said collecting means, and
   a processor (40) connected to said capturing means for analyzing said captured plurality of shadow edge images for the presence of any of said defects.

2. The instrument of claim 1 wherein said directing means collimates said reflected light.

3. The instrument of claim 1 wherein said reflecting means comprises a pair of flat mirrors.

4. The instrument of claim 1 wherein said directing means comprises a pair of plano-convex lenses.

5. The instrument of claim 1 wherein said providing means comprises a pair of cylindrical lenses.

6. A portable shock-proof instrument for determining the presence of defects on the surface of a container, said instrument comprising:
   a housing (20),
   an optical table (200) shock-mounted in said housing, said table comprising:
   a. means (216, 224, 226) for producing a point source of light (220*a*),
   b. means (M1, M2) receptive of said light from said point source for reflecting said light in an inverted U-shaped path so that the first portion of said path of light is directed upwardly, the middle portion of said path is directed horizontally in the top area of said housing, and the third portion of said path is directed downwardly,
   c. means (L1, L2) for collimating said reflected light in said middle portion of said path, said collimating means directing said collimated light (220*b*) past the edge of said container thereby producing a shadow image of said edge,
   d. means (270, 90, 460, 272, 282) firmly holding said container for rotating said container through a predetermined number of positions,
   e. means (CYL 1-2, F, R) receptive of said light in said third portion of said path for providing (220*d*) a predetermined degree of magnification in the horizontal field of view of said container in order to enhance the detection of any defects on the surface of said container, said providing means being further capable of capturing substantially all of said light from said point source and reimaging said shadow image to infinity,
   f. a camera (260) for capturing a plurality of said shadow edge images from said providing means as said container is being rotated by said rotating means, wherein one shadow edge image for each of said predetermined positions of said container is captured, and
   a processor (40) connected to said rotating means and to said camera for analyzing said captured plurality of shadow edge images for the presence of any of said defects.

7. The instrument of claim 6 wherein said providing means further comprises:
   a pair of cylindrical lenses (CYL 1-2) receptive of said light in said third portion of said path for causing (220*d*) said predetermined degree of magnification in the horizontal field of view of said container in order to enhance the detection of any defects on the surface of said container,
   a relay lens (R) for receiving a real image of the shadow edge of said container from said cylindrical lenses, and
   a field lens (F) receiving said real shadow edge image from said relay lens for reimaging said shadow edge image to infinity.

8. A portable shock-proof instrument for determining the surface profile of a container, said instrument comprising:
   a housing (20),
   an optical table (200) shock-mounted in said housing,
   means (216, 224 226) on said table for producing a point source of light (220*a*),
   means (M1, M2) on said table receptive of said light from said point source for reflecting said light in an inverted U-shaped path so that the middle portion of said path is directed horizontally in the top area of said housing,
   a first lens (L1) on said table for collimating said reflected light in said middle portion, said first lens directing said collimated light (220*b*) past the edge of said container thereby producing a shadow image of said edge,
   means (270, 90, 460, 272, 280) on said table and firmly holding said container for rotating said container through a predetermined number of positions,
   means (60, 110) in said housing for permitting the insertion and removal of said container from said rotating means, a second lens (L2) on said table for focusing (220c) in said middle portion said collimated light from said first lens (L1), a pair of cylindrical lenses (CYL 1-2) on said table receptive of said focused light from said second lens for providing (220d) a predetermined degree of magnification in the horizontal field of view of said container, a dust-tight housing mounted on said table, said dust-tight housing comprising:
  a. a relay lens (R) for receiving a real image of the shadow edge of said container from said pair of cylindrical lenses, and
  b. a field lens (F) for receiving said real shadow edge image from said relay lens for reimaging said shadow edge image to infinity, a camera (260) on said table for capturing a plurality of said shadow edge images from said field lens as said container is being rotated by said rotating means, wherein one shadow edge image for each of said predetermined portions of said container is captured, and a processor (40) connected to said holding means and to said camera for processing said captured plurality of shadow edge images into said surface profile.

9. The instrument of claim 8 wherein said holding means comprises:
  means (270, 90, 280) firmly holding said container for rotating said container, and
  means (460, 272) on said table and engaging said rotating means for determining the position of said container as said container is being rotated through a predetermined number of positions.

10. A portable shock-proof instrument for determining the surface profile of a container, said instrument comprising:
  a housing (20),
  an optical table (200) shock-mounted vertically in said housing, said optical table being mounted on at least four horizontal shock-mounts (202a-d) and on at least two vertical shock-mounts (202e-f) to the inside of said housing,
  means (216, 224, 226) on said table for providing a point source of light (220a) directed vertically upwardly in said housing,
  a first mirror (M1) on said table receptive of said light from said point source for reflecting said light by substantially ninety degrees so that said reflected light is directed horizontally in said housing,
  a first lens (L1) on said table for collimating said reflected light from said first mirror, said first mirror directing said collimated light (220b) past the edge of said container thereby producing a shadow image of said edge,
  means (270, 90) on said table and holding said container for rotating said container,
  means (60, 110) in said housing for permitting the insertion and removal of said container from said rotating means,
  means (280) in said housing and connected to said rotating means for providing a vacuum to firmly hold said container to said rotating means,
  means (460, 272) on said table and engaging said rotating means for determining the position of said container as said container is being rotated through a predetermined number of positions,
  a second lens (L2) on said table for focusing (220c) said collimated light from said first lens (L1),
  a second mirror (M2) on said table receptive of said light from said second lens for reflecting said light by substantially ninety degrees so that the aforesaid reflected light is directed downwardly in said housing,
  a pair of cylindrical lenses (CYL 1-2) on said table receptive of said reflected light from said second mirror for providing (220d) a predetermined degree of magnification in the horizontal field of view of said container,
  a dust-tight housing (240) mounted on said table, said dust-tight housing comprising:
    a. a window (W3) placed in a side of said dust-tight housing and substantially located at the focus of said second lens (L2) for extending said light from said cylindrical lenses internally to said dust-tight housing,
    b. a relay lens (R) for receiving a real image of the shadow edge of said container, and
    c. a field lens (F) located in a side of said dust-tight housing for receiving said real shadow edge image from said relay lens for reimaging said shadow edge image to infinity,
  a camera (260) on said table for capturing a plurality of said shadow edge images from said field lens as said container is being rotated by said rotating means, wherein one shadow edge image for each of said predetermined positions of said container is captured,
  a processor (140) connected to said determining means and to said camera for processing said captured plurality of shadow edge images into said surface profile.

11. A portable, shock-proof instrument for determining the presence of dents from the surface profile of an object, said instrument comprising:
  a housing (20),
  an optical table (200) shock-mounted in said housing, said table comprising:
    a. means (216, 224, 226) for providing a source of light (220a),
    b. means (L1, L2) for directing said light (220b) past the edge of said object thereby producing a shadow image of said edge,
    c. means (270, 90, 460, 272, 282) firmly holding said object for rotating said object through a predetermined number of positions,
    d. means (CYL 1-2, F, R) receptive of said light for capturing all of said light from said source means including said shadow image of said edge,
    e. a camera (260) for capturing a plurality of said shadow edge images from said providing means as said object is being rotated by said rotating means, wherein one shadow edge image for each of said predetermined positions of said object is captured, and
  a processor (40) connected to said rotating means and to said camera for analyzing said captured plurality of shadow edge images for the presence of any said dents in said surface profile resulting from said plurality of captured images.

12. The instrument of claim 11 wherein said processor determines the location, periphery, and area of each dent in said object which exceeds a predetermined rate of change in said profile.

13. The instrument of claim 12 wherein said processor evaluates a block of pixels for cross block differences exceeding said predetermined rate of change and when a cross block difference is exceeded said processor places a pattern of markers in a corresponding block indicative of said location, periphery, and area of each said dent.

14. The instrument of claim 11 wherein said profile comprises rows of data and processor inserts into said surface profile of said object a preselected number of additional rows of data above and below the rows of data derived from said captured shadow image of said edge in order to increase the accuracy of said determination, said preselected number being ascertained from the size of a "n ×n" spatial filter:

$$r = (n-1)/2$$

where
  r = said preselected number of rows
  n = the size of said filter,
  said processor copying the pixel values in the upper row of said surface profile into said preselected rows above said profile and said processor copying the pixel values in said lower row of said surface profile into said preselected lower rows below said profile.

15. An instrument for determining the presence of dents from the surface profile of an object, said instrument comprising:
  means (216, 224, 226) for providing a source of light (220a),
  means (L1, L2) for directing said light (220b) past the edge of said object thereby producing a shadow image of said edge,
  means (270, 90, 460, 272, 282) firmly holding said object for rotating said object through a predetermined number of positions,
  means (CYL 1-2, F, R) receptive of said light for capturing all of said light from said source means including said shadow image of said edge,
  a camera (260) for capturing a plurality of said shadow edge images from said providing means as said object is being rotated by said rotating means, wherein one shadow edge image for each of said predetermined positions of said object is captured, and
  a processor (40) connected to said rotating means and to said camera for analyzing said captured plurality of shadow edge images for the presence of any said dents in said surface profile resulting from said plurality of captured images, said processor then being capable of determining the location, periphery, and area of each dent in said object which exceeds a predetermined rate of change in said profile.

16. The instrument of claim 15 wherein said processor evaluates a block of pixels for cross block differences exceeding said predetermined rate of change and when a cross block difference is exceeded said processor places a pattern of markers in a corresponding block indicative of said location, periphery, and area of each said dent.

17. The instrument of claim 15 wherein said profile comprises rows of data and processor inserts into said surface profile of said object a preselected number of additional rows of data above and below said rows of data derived from said captured shadow image of said edge in order to increase the accuracy of said determination, said preselected number being ascertained from the size of a "n ×n" spatial filter:

$$r = (n-1)/2$$

where
  r = said preselected number of rows
  n = the size of said filter,
  said processor copying the pixel values in the upper row of said surface profile into said preselected rows above said profile and said processor copying the pixel values in said lower row of said surface profile into said preselected lower rows below said profile.

18. An instrument for determining the presence of defects from the surface profile of an object, said instrument comprising:
  means (216, 224, 226) for providing a source of light (220a),
  means (L1, L2) for directing said light (220b) past the edge of said object thereby producing a shadow image of said edge,
  means (270, 90, 460, 272, 282) firmly holding said object for rotating said object through a predetermined number of positions,
  means (CYL 1-2, F, R) receptive of said light for capturing all of said light from said source means including said shadow image of said edge,
  a camera (260) for capturing a plurality of said shadow edge images from said providing means as said object is being rotated by said rotating means, wherein one shadow edge image for each of said predetermined positions of said object is captured, and
  a processor (40) connected to said camera for analyzing said captured plurality of shadow edge images for the presence of any said defects in said surface profile resulting from said plurality of captured images, said surface profile comprising rows of data, said processor being further capable of inserting into said surface profile of said object a preselected number of additional rows of data above and below said rows of data derived from said captured shadow image of said edge in order to increase the accuracy of said analyses, said preselected number being ascertained from the size of a "n ×n" spatial filter being used for said analysis:

$$r = (n-1)/2$$

where
  r = said preselected number of rows
  n = the size of said filter,
  said processor copying the pixel values in the upper row of said surface profile into each of said preselected number of rows above said profile and said processor copying the pixel values in said lower row of said surface profile into each of said preselected number of lower rows below said profile.

* * * * *